(12) United States Patent
Munoz

(10) Patent No.: US 6,372,007 B1
(45) Date of Patent: Apr. 16, 2002

(54) ORGANIC COMPOST

(75) Inventor: Antonio Munoz, 6300 W. Little York, #112 Houston, TX (US) 77091

(73) Assignees: Rafael Munoz; Jose Munoz; Clotilde Munoz; Antonio Munoz, all of Houston, TX (US)

( * ) Notice: Subject to any disclaimer, the term of this patent is extended or adjusted under 35 U.S.C. 154(b) by 0 days.

(21) Appl. No.: 09/491,736

(22) Filed: Jan. 27, 2000

Related U.S. Application Data
(60) Provisional application No. 60/117,912, filed on Jan. 29, 1999, and provisional application No. 60/131,285, filed on Apr. 27, 1999.

(51) Int. Cl.$^7$ ................................................. C05F 3/00
(52) U.S. Cl. .................... 71/15; 71/24; 71/54; 71/55; 71/56; 71/57; 71/58; 71/59; 71/61
(58) Field of Search ................................ 71/15, 24, 54, 71/55, 56, 57, 58, 59, 61

(56) References Cited

U.S. PATENT DOCUMENTS

| 3,674,649 A | | 7/1972 | Formisano et al. .......... 195/104 |
| 4,127,964 A | | 12/1978 | Mee ............................... 47/1.1 |
| 4,193,786 A | * | 3/1980 | Brill ................................. 71/9 |
| 4,218,233 A | * | 8/1980 | Hackett ............................ 71/9 |
| 4,752,316 A | | 6/1988 | Plovanich et al. ................ 71/9 |
| 5,393,317 A | | 2/1995 | Robinson ......................... 71/12 |

FOREIGN PATENT DOCUMENTS

| FR | 2141588 | | 6/1971 |
| GB | 2037730 | * | 7/1980 |

\* cited by examiner

*Primary Examiner*—Chhaya D. Sayala

(57) ABSTRACT

The present invention relates generally to organic compost used to treat soil. The compost serves as a source of plant nutrients, improves soil structure, encourages the growth of beneficial microorganisms and can be used as a vehicle in the formulation of other soil treatment compounds.

8 Claims, No Drawings

ORGANIC COMPOST

This application claims the benefit of U.S. Provisional Application No. 60/117,912, filed on Jan. 29, 1999 and U.S. Provisional Application No. 60/131,285, filed on Apr. 27, 1999, the disclosures of which are incorporated herein by reference.

BACKGROUND OF THE INVENTION

1. Field of the Invention

The invention relates generally to organic compost used to treat soil. The compost serves as a source of plant nutrients, improves soil structure, encourages the growth of beneficial microorganisms and can be used as a vehicle in the formulation of other soil treatment compounds.

2. Description of the Related Art

A number of organic soil conditioners have been described previously. In one, peat moss is treated with an alkaline solution to form a humic acid salt. A strong acid is then added to the solution to precipitate the salt. The humic acid salt and a fulvic acid solution can then be coagulated to form flocs. These flocs are dried and applied to the soil as a conditioner.

In a second organic soil conditioner, cold manure is combined with naturally occurring humic acid and a small amount of inorganic material, such as gypsum. The inorganic material enhances the permeability of the compost, which is used to stimulate the growth of mushrooms.

A third organic soil enhancer is made from composted hardwood bark, composted pine bark or composted sewage sludge. This soil enhancer suppresses disease caused by *Rhizoctonia solani* and *Pythium ultimum*.

SUMMARY OF THE INVENTION

The present invention relates to a method of making organic compost. Bovine manure is obtained and incubated under aerobic conditions. The incubated manure is dried, pasteurized and ground into powder. A source of humic acid and nitrogen may be mixed in to form a homogenous mixture. The compost may be used to treat soil.

DETAILED DESCRIPTION OF THE PREFERRED EMBODIMENT

Traditional fertilizers can cause problems in the soil and plants to which they are applied, as well as in the environment generally. Because traditional fertilizers are often soluble salts, excessive application can lead to accumulation in the soil and germination problems or even plant death. In addition fertilizer carried in ground water or surface water can contaminate streams, rivers and lakes.

The present invention describes a non-toxic organic compost which can be used to treat the soil in which plants are grown. The invention is in powder form and thus diffuses easily into the soil. Because it is readily incorporated into the soil, there is a decreased probability that runoff waters will carry the compost away. Thus the compost does not migrate into areas which do not require soil treatment or in which the presence of the compost would be problematic.

When used to treat soil, the compost of the present invention provides nitrogen and other essential nutrients directly to plants. In addition, the compost acts indirectly by flocculating soil particles. This causes the release of previously fixed nutrients, thus making them available to plants. The nutrients provided by the application of the compost are also beneficial to soil microflora that can act as biological pesticides to control soil-borne pathogens.

Further, application of the compost improves soil structure by increasing soil aeration and the capacity of the soil to retain water. The compost also increases soil temperature so that the plants grown in the soil become active earlier in the season.

The compost may also serve as a vehicle in the formulation of other soil treatment compounds. For example, an active, beneficial microorganism may be mixed into the compost prior to application. The nutrients provided by the compost help ensure the activity of the microorganism. Similarly, any soil additive or combination of additives may be mixed with the compost to provide a customized soil treatment compound.

The compost of the present invention is prepared from dry cow manure. High quality bovine manure is first obtained. The manure is then incubated under aerobic conditions, preferably until fermentation is completed. In the preferred embodiment, the manure is spread so that it is approximately 1.5 m wide and 1.0 m in height. The manure is heated to 70–75° C. The manure is turned twice a day for 1–2 days. After this period, the mixture is turned once a day for 4 additional days. If the mixture gets too hot, water can be added to cool it down.

After incubation, the manure is dried. In the preferred embodiment, the manure is spread outdoors in a row 3 m wide and approximately 20 cm high until it dries. However, any method of drying known in the art may be employed.

In the preferred embodiment, after drying the manure is pasteurized by any method known in the art. The pasteurized manure is then ground to a powder form.

The resulting powder may make up from 50 to 100% of the compost of the present invention. In the preferred embodiment the powder makes up 97% of the compost of the present invention. Additionally, in the preferred embodiment a source of nitrogen and humic acids are added to the powder. These components can be obtained from any source known in the art. All components are then mixed together to form a homogeneous mixture, the compost of the present invention.

In the preferred method the compost is used to treat soil in which plants are growing or are to be grown. Preferably, the compost is applied in the amount of from 10 to 1000 grams per square foot of soil every 2 to 12 months. More preferably, the compost is applied in the amount of 110 grams per square foot of soil every 4 months. The compost is applied to the soil by dusting. In a typical use of the product on soil in which sod is growing, results will be observed 30 days after the application and during the following three months. There will be an improvement in soil texture and fertility and an increase in moisture retention. The sod will look greener and grow faster, thicker and more vigorously as a result of the improved plant nutrition provided by the application of the compost.

The compost of the present invention is harmless to humans and domestic animals and there is no limitation on the types of plants that can be grown in soil that has been treated with it. The compost of the present invention is effective on field crops such as corn, snapbeans, sorghum, peas and cotton. It is also effective on vegetables such as peppers, tomatoes, cantaloupes, and potatoes, on perennial fruits trees such as pecan, citrus, apples, on annual fruits such as bananas and strawberries, and on ornamental plants such as turf, oak, magnolia and bougainvillea.

EXAMPLE 1

A sample of the compost of the present invention was subject to chemical analysis.

| PERCENTAGE (DRY WEIGHT) | % | lb/ton | |
|---|---|---|---|
| Total Nitrogen (N) | 8.96 | 179.2 | |
| Soluble Nitrate (NO$_3$) | 0.39 | 7.89 | |
| Total Phosphorus (P) | 1.29 | 59.11 | P$_2$O$_5$ |
| Soluble Phosphate (PO$_4$) | 0.63 | 12.66 | |
| Potassium (K) | 2.78 | 67.00 | K$_2$O |
| Sodium (Na) | 0.80 | 16.00 | |
| Calcium (Ca) | 3.92 | 78.40 | |
| Magnesium (Mg) | 1.25 | 25.00 | |
| Zinc (Zn) | 0.0220 | 0.44 | |
| Iron (Fe) | 0.1500 | 3.00 | |
| Manganese (Mn) | 0.0328 | 0.66 | |
| Copper (Cu) | 0.0038 | 0.08 | |
| Boron (B) | 0.0010 | 0.02 | |

What is claimed is:

1. A method of making organic compost comprising:

obtaining bovine manure;

incubating the manure under aerobic conditions;

drying the incubated manure;

pasteurizing the dried manure; and grinding the pasteurized manure into powder.

2. The method of claim 1, additionally comprising adding a source of humic acid to said powder.

3. The method of claim 2, additionally comprising mixing to form a homogenous mixture.

4. The method of claim 2, additionally comprising adding a source of nitrogen to said powder.

5. The method of claim 4, additionally comprising mixing to form a homogenous mixture.

6. A method of treating soil comprising:

applying the compost of claim 1 to soil.

7. The method of claim 6 wherein 110 g is applied per square foot of soil.

8. The method of claim 6 wherein said application is repeated every 4 months.

* * * * *